United States Patent
Casey et al.

(10) Patent No.: US 12,071,661 B2
(45) Date of Patent: Aug. 27, 2024

(54) METHOD OF PREDICTING RESPONSE TO THERAPY BY ASSESSING TUMOR GENETIC HETEROGENEITY

(71) Applicant: Roche Sequencing Solutions, Inc., Pleasanton, CA (US)

(72) Inventors: Fergal Casey, Pleasanton, CA (US); John J. Lee, Walnut Creek, CA (US); John F. Palma, Alamo, CA (US); Stephanie J. Yaung, San Jose, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 890 days.

(21) Appl. No.: 16/968,811

(22) PCT Filed: Feb. 11, 2019

(86) PCT No.: PCT/EP2019/053272
§ 371 (c)(1),
(2) Date: Aug. 10, 2020

(87) PCT Pub. No.: WO2019/155050
PCT Pub. Date: Aug. 15, 2019

(65) Prior Publication Data
US 2021/0002719 A1  Jan. 7, 2021

Related U.S. Application Data

(60) Provisional application No. 62/629,635, filed on Feb. 12, 2018.

(51) Int. Cl.
*C12Q 1/6869* (2018.01)
*A61K 31/4745* (2006.01)
*G16H 50/30* (2018.01)

(52) U.S. Cl.
CPC ........ *C12Q 1/6869* (2013.01); *A61K 31/4745* (2013.01); *G16H 50/30* (2018.01); *C12Q 2600/158* (2013.01)

(58) Field of Classification Search
CPC . C12Q 1/6869; C12Q 2600/156; G16H 50/30
See application file for complete search history.

(56) References Cited

FOREIGN PATENT DOCUMENTS

| CN | 106676178 A | 5/2017 | |
|---|---|---|---|
| EP | 3153591 A1 | 4/2017 | |
| WO | 2008/100913 A2 | 8/2008 | |
| WO | 2010/145796 A2 | 12/2010 | |
| WO | 2011/011767 A1 | 1/2011 | |
| WO | WO-2014055635 A1 * | 4/2014 | ............ G06F 19/18 |
| WO | 2015/031808 A2 | 3/2015 | |
| WO | 2016/040901 A1 | 3/2016 | |

OTHER PUBLICATIONS

Roche. "Roche launches AVENIO ctDNA Kits for Oncology Research" 2017. Retrieved on Aug. 23, 2023 from the internet: assets.roche.com/imported/en/med-cor-2017-05-08-e.pdf. (Year: 2017).*
NCT01765582. Retrieved on Aug. 23, 2023 from the internet: https://classic.clinicaltrials.gov/ct2/show/study/NCT01765582. (Year: 2023).*
Jiang et al. Journal of Thoracic Oncology. 2017. 12(11S2):OA 10.06. (Year: 2017).*
Frenel J S et al., Serial Next-Generation Sequencing of Circulating Cell-Free DNA Evaluating Tumor Clone Response To Molecularly Targeted Drug Administration, Clin Canc Res, (2015), pp. 4586-4596, vol. 21 Issue 20.
Iijima, Y. et al., Very early response of circulating tumour-derived DNA in plasma predicts efficacy of nivolumab treatment in patients with non-small cell lung cancer, European Journal of Cancer, (2017), pp. 349-357, vol. 86.
International Preliminary Report on Patentability, mailed Aug. 18, 2020, in corresponding PCTEP2019053272, filed Feb. 11, 2019, pp. 1-10.
International Search Report and Written Opinion, mailed Apr. 30, 2019, in corresponding PCTEP2019053272 filed Feb. 11, 2019 pp. 1 to 17.
Murtaza M et al., Multifocal clonal evolution characterized using circulating tumour DNA in a case of metastatic breast cancer, Nat Commun, (2015), pp. 1-6, vol. 6 Issue 1.
Perdigones, N. et al, Capturing tumor heterogeneity and clonal evolution in solid cancers using circulating tumor DNA analysis, Pharmacology & Therapeutics, (2017), pp. 22-26, vol. 174.
Rajput A et al., Mutant-Allele Tumor Heterogeneity Scores Correlate With Risk of Metastases in Colon Cancer, Clin Color Cancer, (2017), pp. e165-e170, vol. 16.
Ulz, P. et al, Patient monitoring through liquid biopsies using circulating tumor DNA, International Journal of Cancer, (2017), pp. 887-896, vol. 141, Issue 5.
Vidal J. et al, Plasma ctDNA RAS mutation analysis for the diagnosis and treatment monitoring of metastatic colorectal cancer patients, Annals of Oncology, (2017), pp. 1325-1332, vol. 28, Issue 6.
Yang M. et al, Circulating mutational portrait of cancer: manifestation of aggressive clonal events in both early and late stages, Journal of Hematology & Oncology, (2017), pp. 1-13, vol. 10, Art. No. 100.
Yi X et al., The feasibility of using mutation detection in ctDNA to assesstumor dynamics, Int J Cancer, (2017), pp. 2642-2647, vol. 140 Issue 12.
Roche launches AVENIO ctDNA Analysis Kits forOncology Research, Media Release,-, pp. 1-4, (2017).
AVENIO, ctDNA expanded kit, Brochure,-, SEQ100047, (2016).
Hoffmann, F et al., Roche launches AVENIO ctDNA Analysis Kits for Oncology Research, India Pharma News,-, https://www.roche.com/dam/jcr:c6ecf4b7-6d24-48cb-8458-510ed0798625/en/med-cor-2017-05-08-e.pdf, (2017).

(Continued)

*Primary Examiner* — Joseph G. Dauner
(74) *Attorney, Agent, or Firm* — Daniel E. Agnew

(57) ABSTRACT

The invention is a method of predicting response to therapy in a colorectal cancer patient, the method comprising measuring tumor genetic heterogeneity via analysis of circulating tumor DNA from a patients sample.

5 Claims, 11 Drawing Sheets

(56) References Cited

OTHER PUBLICATIONS

Kato, K et al., Numerical indices based on circulating tumor DNA for the evaluation of therapeutic response and disease progression in lung cancer patients, Scientific Reports, vol. 6 Issue 1, pp. 29093, (2016).

Kikuya Kato et al., Numerical indices based on circulating tumor DNA for the evaluation of therapeutic response and disease progression in lung cancer patients, journal, N/A, Jul. 6, 2016.

Newman, A et al., An ultrasensitive method for quantitating circulating tumor DNA with broad patient coverage, Nat Med, vol. 20 Issue 5, pp. 548-554, (2014).

Newman, A. M. et al, Integrated digital error suppression for improved detection of circulating tumor DNA, Nature Biotechnology, vol. 34, No. 5, pp. 547-555, (2016).

Roche, Avenio ctDNA Surveillance Kit coverage for lung and CRC serial tumor burden monitoring, Tumor Burden Monitoring,-, retrieved from the Internet, Jul. 31, 2017.

* cited by examiner

METHOD OF PREDICTING RESPONSE TO THERAPY BY ASSESSING TUMOR GENETIC HETEROGENEITY

FIELD OF THE INVENTION

The invention relates to the field of oncology. More specifically, the invention relates to the field of nucleic acid-based testing of cancer patients.

BACKGROUND OF THE INVENTION

Many of the colorectal cancer (CRC) patients are diagnosed with metastatic disease after progression from earlier stage disease. At that time, prognosis is poor and the optimal choke of effective therapy is critical. Currently, mCRC patients receive either targeted anti-EGFR therapy plus chemotherapy based on RAS wildtype status or all corners are eligible for anti-angiogenesis plus chemotherapy. Traditionally, a surgical specimen could be tested for the presence of a mutation. Modern diagnostic approaches rely on mutations found in circulating tumor DNA (ctDNA) to predict tumor resistance and recurrence. For example, increasing mutant allele frequencies (AF) of resistance mutations indicate developing resistance to a particular targeted therapy. There is however a need for a more general assessment of tumor evolution from pre- to post-treatment in order to select the appropriate therapy.

SUMMARY OF THE INVENTION

In some embodiments, the invention is a method for identifying a cancer patient as likely to positively respond to a therapy regimen, the method comprising the steps of: providing samples obtained from the patient comprising at least one solid tumor sample and at least one blood plasma sample; determining in the samples the sequence of at least a portion of each of the biomarkers listed in Table 1; determining a measure of genetic heterogeneity in the biomarker sequence, the measure of heterogeneity selected from plasma recovery rate (PRR), mutant allele tumor heterogeneity (MATH) and multi-variant gene count (MVGC); identifying the patient as likely to positively respond to a therapy regimen if the measure of genetic heterogeneity is low; or identifying the patient as not likely to positively respond to a therapy regimen if the measure of genetic heterogeneity is high. The cancer may be non-small cell lung cancer (NSCLC) or colorectal cancer (CRC) in stages I, II, if I or IV. The positive response to therapy may be increased progression free survival (PPS) or increased overall survival (OS). The therapy regimen may be treatment with FOLFOXIRI-bevacizumab and treatment FOLFOX-bevacizumab, concurrent or sequential.

In some embodiments, the measure of genetic heterogeneity is tissue-plasma concordance measured as one or more of plasma recovery rate (PRR), tissue recovery rate (TRR) and Jaccard index (JI). For PRR, high heterogeneity is PRR=0, low heterogeneity is PRR=1, and intermediate heterogeneity is 0<PRR<1. PRR may be determined as a ratio of shared plasma and matched tissue variants to total plasma variants.

In some embodiments, the measure of genetic heterogeneity is mutant allele tumor heterogeneity (MATH). High heterogeneity may be MATH above median, in the top tertile or in the top quartile. MATH may be determined according to Formula 1 or be chromosome weighted MATH (cw-MATH), e.g., determined according to Formula 2.

In some embodiments, the measure of genetic heterogeneity is multi-variant gene count (MVGC) and high heterogeneity is MVCG>0 and low heterogeneity is MVGC=0. MVGC may be determined as a number of genes with multiple mutations.

In some embodiments, the plasma samples are collected during more than one time point pre-during and post-chemotherapy and the measure of genetic heterogeneity is compared between time points and the genetic heterogeneity is high if the comparison detects an increase between time points.

In some embodiments, the measure of genetic heterogeneity is the presence of gene truncations, e.g., in APC, TP33 or FBXW7. The presence of gene truncations may be measured only in post-therapy plasma.

In some embodiments, the invention is a method of treatment of a non-small cell lung cancer (NSCLC) or colorectal cancer (CRC) patient in stage II, III or IV comprising the steps of providing samples obtained from the patient comprising at least one solid tumor sample and at least one blood plasma sample; determining in the samples the sequence of at least a portion of each of the biomarkers listed in Table 1; determining a measure of genetic heterogeneity in the biomarker sequence, the measure of heterogeneity selected from plasma recovery rate (PRR), mutant allele tumor heterogeneity (MATH) and multi-variant gene count (MVGC); identifying the patient as likely to positively respond to a less aggressive therapy regimen if the measure of genetic heterogeneity is low and administering the less aggressive therapy regimen; or identifying the patient as not likely to positively respond to a less aggressive therapy regimen if the measure of genetic heterogeneity is high and administering a more aggressive therapy regimen. The more aggressive therapy regimen may be a higher dose of therapy, addition of one or more therapeutic agents, and extended duration of therapy as compared to the less aggressive therapy regimen.

In some embodiments, the invention is a computer system designed to implement an algorithm for determining a measure of genetic heterogeneity of a cancer in a patient, wherein the algorithm analyses sequencing data on one or more as biomarkers obtained from the patient's sample and contains one or more steps selected from mutation detection, mutation frequency scoring, error correction, final determination whether the sample is mutation-positive and a step of determining a value selected from plasma recovery rate (PRR), mutant allele tumor heterogeneity (MATH), and multi-variant gene count (MVGC) to determine genetic heterogeneity of the cancer.

In some embodiments, the invention is a computer system designed to implement an algorithm for selecting a therapy for a cancer patient by determining a measure of genetic heterogeneity of the cancer, wherein the algorithm analyses sequencing data on one or more biomarkers obtained from the patient's sample and contains one or more steps selected from mutation detection, mutation frequency scoring, error correction, final determination whether the sample is mutation-positive and a step of determining a value selected from plasma recovery rate (PRR), mutant allele tumor heterogeneity (MATH), and multi-variant gene count (MVGC) to determine genetic heterogeneity of the cancer and selecting a more aggressive therapy if genetic heterogeneity is high and less aggressive therapy if genetic heterogeneity is low.

In some embodiments, the invention is a method of treatment of a non-small cell lung cancer (NSCLC) or colorectal cancer (CRC) patient in stage II, III or IV comprising the steps of: providing samples obtained from the patient comprising at least one solid tumor sample and at least one blood plasma sample; determining in the samples the sequence of at least a portion of each of the biomarkers listed in Table 1; determining plasma recovery rate (PRR) and administering irinotecan if PRR is high (e.g., =>0.8) and not administering irinotecan if PRR is low (e.g., <0.8).

In some embodiments, the invention is a method of treatment oft non-small cell lung cancer (NSCLC) or colorectal cancer (CRC) patient in stage II, III or IV comprising the steps of providing samples obtained from the patient comprising at least one solid tumor sample and at least one blood plasma sample; determining in the samples the sequence of at least a portion of each of the biomarkers listed in Table 1; determining a measure of genetic heterogeneity in the patient's sample; administering a metastasis-targeting therapy if genetic heterogeneity is high.

DETAILED DESCRIPTION OF THE INVENTION

Definitions

Figure 1:
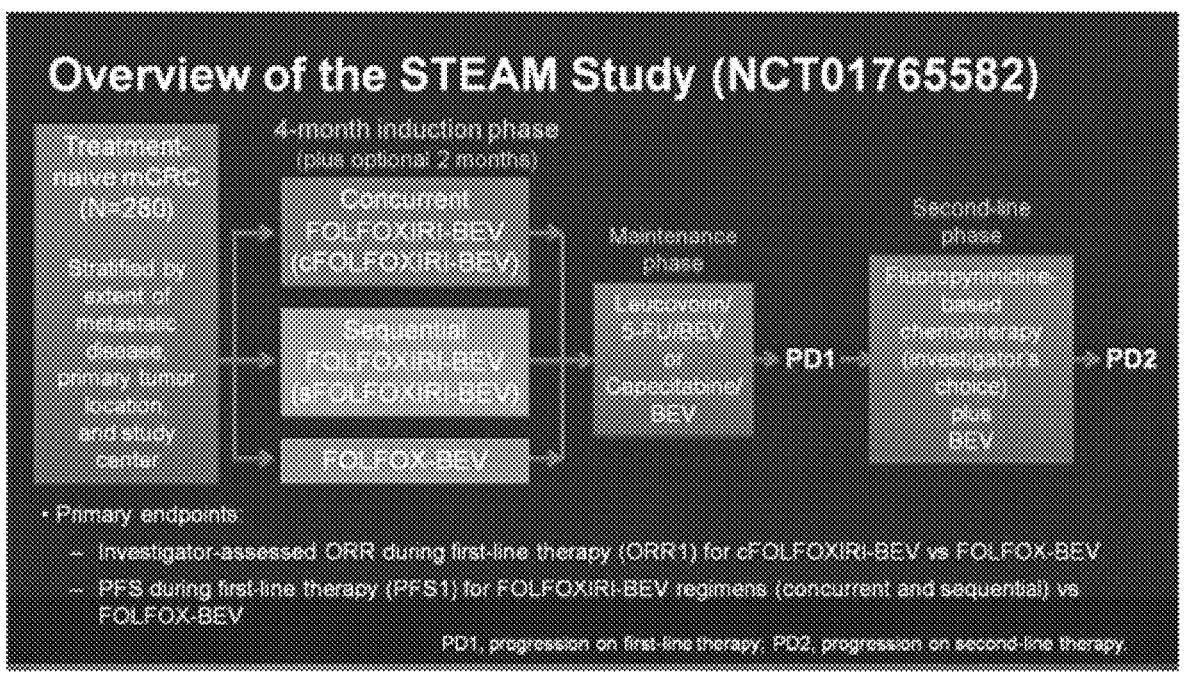
FIG. 1 illustrates the design of the therapy response prediction study (STEAM trial).

The following definitions are not limiting but merely aid in understanding this disclosure.

The term "PFS" is used herein to describe the time of Progression Free Survival for a patient.

The term "OS" is used herein to describe the time of Overall Survival for a patient.

The term "circulating tumor DNA (ctDNA)" is used herein to describe a portion of cell-free DNA (cDNA) found in human blood plasma or serum that originates from the tumor. Circulating tumor DNA is distinguished from non-tumor DNA by the mutations characteristic of the tumor.

The term "biomarker" Is used herein to describe a nucleotide sequence that contains information relevant to the biological or clinical phenomenon. For example, the information may be a mutation status of the nucleotide sequence. The biomarker can be a gene (including coding sequence, regulatory sequence, intron or a splice site) or an intergenic region. The clinical phenomenon can be the presence of malignant cells, e.g., tumor cells in a patient's sample.

The invention describes methods of selecting a treatment regimen for a non-small cell lung cancer (NSCLC) patient or a colorectal cancer (CRC) patient including a metastatic colorectal cancer (mCRC) patient.

In some embodiments, the invention uses a biomarker panel to identify somatic mutations and mutation burden in cancer-related genes by next-generation sequencing (NGS). In some embodiments, the invention utilized a blood or blood-derived sample from a patient. The sample can include any fraction of blood. e.g., serum or plasma, which contains cell-free DNA including circulating tumor DNA (cfDNA or ctDNA). In some embodiments, the sample is taken serially at various times during treatment, e.g., before and after surgery or before, after and during a chemotherapy regimen. In some embodiments, a tumor sample such as a solid tumor sample is used for comparison with the blood sample. The solid tissue or blood sample can be collected by a suitable means that preserves the DNA therein, including formalin-fix paraffin-embedding (FFPE), fresh frozen tissue or blood tissue collected in a preservative medium.

In some embodiments, the invention utilizes a biomarker panel, including a gene panel or a mutation panel or a somatic variant panel. The mutations may include single-nucleotide variations (SNVs), deletions and insertions (indels) that correspond to non-sense, missense and frame-shift mutations if they occur in the coding regions of genes. Other types of mutations include gene fusions and translocations. The selection, size and content of such panels has been described e.g., in U.S. patent application Ser. Nos. 14/209, 807, 14/774,518 and International app. No. PCT/US2015/049838 titled "identification and Use of Circulating Tumor Markers." In some embodiments, the invention includes determining the sequence of the biomarkers in the panel, e.g., the genes listed in Table I. In some embodiments, the entire sequence of a gene is determined. In other embodiments, the entire coding sequence of a gene is determined. In other embodiment only the sequence of a portion of the gene known to undergo mutagenesis in cancer is determined. In yet other embodiments, the biomarker is not associated with a coding sequence but is associated with a regulatory sequence or a sequence of unknown function known to be mutated in human tumors.

In the context of the present invention, the sequence of a biomarker can be determined via any suitable method known in the art. The suitable method would have sufficient accuracy, e.g., sensitivity and specificity to detect rare sequences with a low rate of errors. In some embodiments, the sequencing method includes an error correction step, such as use of molecular barcodes, error stereotyping and other chemical or computation methods of error suppression as described e.g., in see the patent applications "Identification and Use of Circulating Tumor Markers", supra. The sequencing method may include a massively parallel sequencing method, including an array based sequencing (ILLUMINA, Inc., San Diego, Cal.), an emulsion-based sequencing (THERMO FISHER SCIENTIFIC, Inc., Waltham, Mass.) an optical measurement based sequencing (PACIFIC BIOSCIENCES of CALIFORNIA, Inc., Menlo Park, Cal.) or a nanopore-based sequencing (ROCHE SEQUENCING SOLUTIONS, Inc., Santa Clara, Cal.).

In some embodiments, the invention utilizes a biomarker panel, such as AVENIO® ctDNA Analysis Kit (Roche Sequencing Solutions, Inc., Pleasanton, Cal.) that is capable of analyzing the tissue and blood of patients to identify and quantity tumor specific mutations in the samples. The composition of the biomarker panel in AVENIO® ctDNA Analysis Kit (expanded panel) is shown in Table 1. The composition of the biomarker panel in AVENIO® ctDNA Analysis Kit (surveillance panel) is shown in Table 2.

TABLE 1

Composition of the expanded biomarker panel

| | | | | | |
|---|---|---|---|---|---|
| APC | KRAS | ABL1 | FGFR3 | JAK3 | RAF1 |
| BRCA1 | MET | AKT1 | FLT1 | KDR | RNF43 |
| BRCA2 | TP53 | AKT2 | FLT3 | MAP2K1 | TERT promoter |
| EGFR | KIT | ARAF | FLT4 | MAP2K2 | TSC1 |
| ERBB2 | NRAS | CDK6 | GATA3 | MTOR | TSC2 |
| ALK | PDGFRA | CSF1R | GNA11 | NFE2L2 | PTEN |
| BRAF | RET | CTNNB1 | GNAQ | NTRK1 | RB1 |
| DPYD | ROS1 | DDR2 | GNAS | PDGFRB | SMAD4 |
| AR | MSH2 | EZH2 | IDH1 | PIK3CA | SMO |
| CCND1 | MSH6 | FGFR1 | IDH2 | PIK3R1 | STK11 |
| CCND2 | NF2 | FGFR2 | JAK2 | PTCH1 | VHL |
| CCND3 | PDCD1LG2 | CDK4 | ESR1 | KEAP1 | UGT1A1 |
| CD274 | PMS2 | CDKN2A | FBXW7 | MLH1 | |

TABLE 2

Composition of the surveillance biomarker panel

| | | | | | | | |
|---|---|---|---|---|---|---|---|
| ABCC5 | CSMD1 | FAT1 | HTR1E | MAP7D3 | PIK3CA | SV2A | |
| ABCG2 | CSMD3 | FBN2 | HTR2C | MKRN3 | PIK3CG | T | |
| ACTN2 | CTNNB1 | FBXL7 | IFI16 | MMP16 | PKHD1L1 | THSD7A | |
| ADAMTS12 | CTNND2 | FBXW7 | IL7R | MTX1 | POLE | TIAM1 | |
| ADAMTS16 | CYBB | FCRL5 | INSL3 | MYH7 | POM121L12 | TMEM200A | |
| ARFGEF1 | DCAF12L1 | FOXG1 | ITGA10 | MYT1L | PREX1 | TNFRSF21 | |
| ASTN1 | DCAF12L2 | FRYL | ITSN1 | NAV3 | PTPLA | TNN | |
| ASTN2 | DCAF4L2 | GBA3 | KCNA5 | NEUROD4 | RALYL | TNR | |
| AVPR1A | DCLK1 | GBP7 | KCNB2 | NFE2L2 | RFX5 | TRHDE | |
| BCHE | DCSTAMP | GJA8 | KCNC2 | NLGN4X | RIN3 | TRIM58 | |
| BPIFB4 | DDI1 | GPR139 | KCNJ3 | NLRP3 | RNASE3 | TRPS1 | |
| C6 | DLGAP2 | GRIA2 | KCTD8 | NMUR1 | ROBO2 | UGT3A2 | |
| C6orf118 | DMD | GRIK3 | KEAP1 | NOL4 | SEMA5B | USH2A | |
| CA10 | DNTTIP1 | GRIN2B | KIAA1211 | NPAP1 | SLC18A3 | USP29 | |
| CACNA1E | DOCK3 | GRIN3B | KIF17 | NR0B1 | SLC39A12 | VPS13B | |
| CDH12 | DSC3 | GRM1 | KIF19 | NRXN1 | SLC6A5 | WBSCR17 | |
| CDH18 | DSCAM | GRM5 | KLHL31 | NXPH4 | SLC8A1 | WIPF1 | |
| CDH8 | EGFLAM | GRM8 | KPRP | NYAP2 | SLITRK1 | WSCD2 | |
| CDH9 | EPHA5 | GSX1 | LPPR4 | OPRD1 | SLITRK4 | ZC3H12A | |
| CDKN2A | EPHA6 | HCN1 | LRFN5 | P2RY10 | SLITRK5 | ZFPM2 | |
| CHRM2 | EYS | HCRTR2 | LRP1B | PAX6 | SLPI | ZIC1 | |
| CNTN5 | FAM135B | HEBP1 | LRRC7 | PCDH15 | SMAD4 | ZIC4 | |
| CNTNAP2 | FAM151A | HECW1 | LRRTM1 | PDYN | SOX9 | ZNF521 | |
| CPXCR1 | FAM5B | HS3ST4 | LRRTM4 | PDZRN3 | SPTA1 | ZSCAN1 | |
| CPZ | FAM5C | HS3ST5 | LTBP4 | PGK2 | ST6GALNAC3 | KIT | |
| CRMP1 | FAM71B | HTR1A | MAP2 | PHACTR1 | STK11 | NRAS | |
| APC | KRAS | ALK | PDGFRA | MET | BRAF | RET | |
| BRCA1 | BRCA2 | TP53 | DPYD | EGFR | ERBB2 | UGT1A1 | |

In some embodiments, the panel of 77 genes listed in Table 1 is used. In some embodiments, the panel of 197 genes listed in Table 2 is used. In some embodiments, the mutation status is determined in both pre-, during and post-chemotherapy plasma samples and the changes are determined. In some embodiments, the mutation status is determined in pre-chemotherapy tumor samples and compared to that of the plasma samples.

The inventor have devised a method of using plasma-based measurements of tumor heterogeneity to prescribe a treatment regimen. In some embodiments, the treatment is selected from a combination of FOLFOXIRI or FOLFOX and bevacizumab (BEV). In some embodiments, the invention is a method of changing the therapy from less aggressive therapy to more aggressive therapy based on the tumor genetic heterogeneity. The more aggressive therapy regimen may comprise one or more of a higher dose of therapy, addition of one or more therapeutic agents, and extended duration of therapy as compared to the less aggressive therapy regimen.

The invention comprises a step of measuring genetic heterogeneity in a patients' sample by analyzing the full profile of somatic mutations in circulating tumor DNA (ctDNA). The inventors obtained unexpectedly good predictive results with ctDNA-called mutations. Not intending to be bound by a particular theory, the inventors hypothesize that the unexpectedly good predictive results are due to the fact that ctDNA might comprise nucleic acids from multiple regions of the primary tumor and from multiple metastatic tumors (including the not yet detectable metastatic tumors). In contrast, the existing methods utilize a tumor biopsy which represents a single region of a single tumor. In some embodiments, the method comprises a step of comparing genetic heterogeneity in tumor and ctDNA from the same patient. In some embodiments, the method comprises a step of comparing genetic heterogeneity in ctDNA samples collected from the same patient and multiple points during the treatment.

In some embodiments, measuring genetic heterogeneity comprises measuring plasma-tissue discordance which can be measured as one or more of Plasma Recovery Rate (PRR). Tissue Recovery Rate (TRR) and Jaccard Index (JI).

Figure 2:
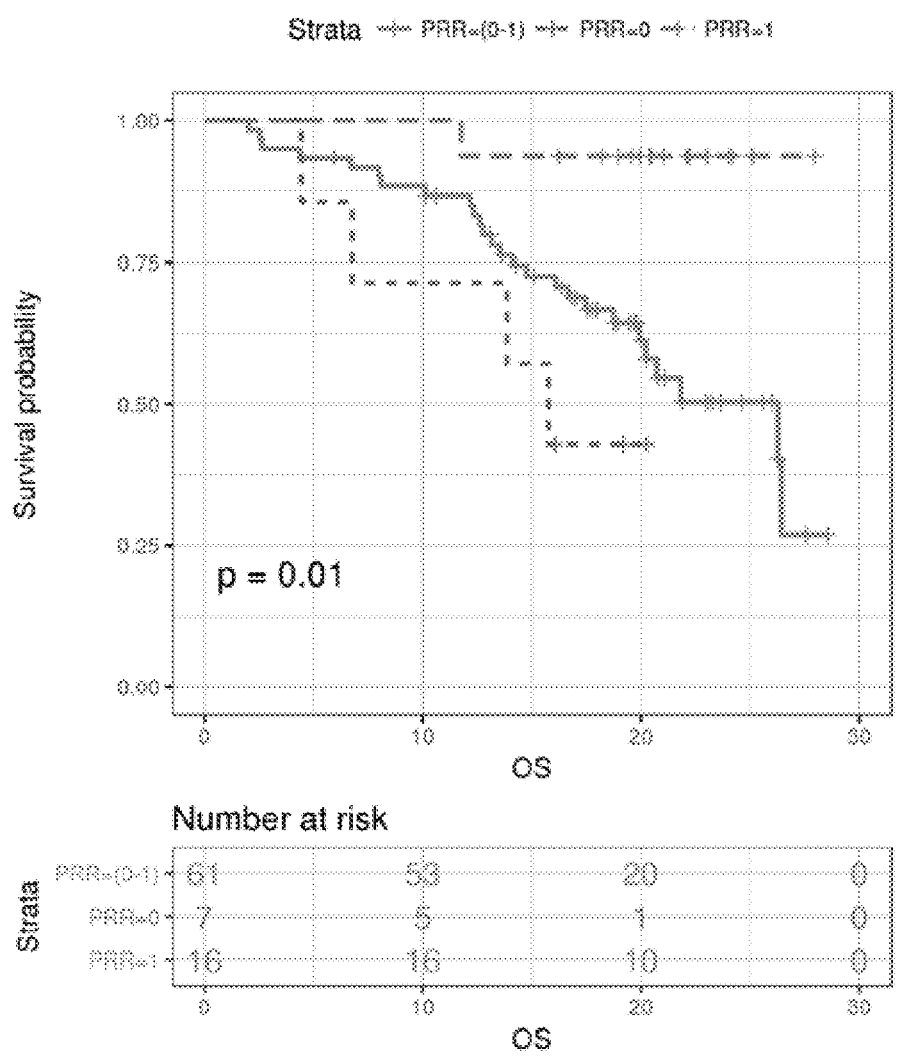
FIG. 2 is a Kaplan Meier graph of overall survival (OS) of patients grouped by plasma recovery rate (PRR).
Figure 3:
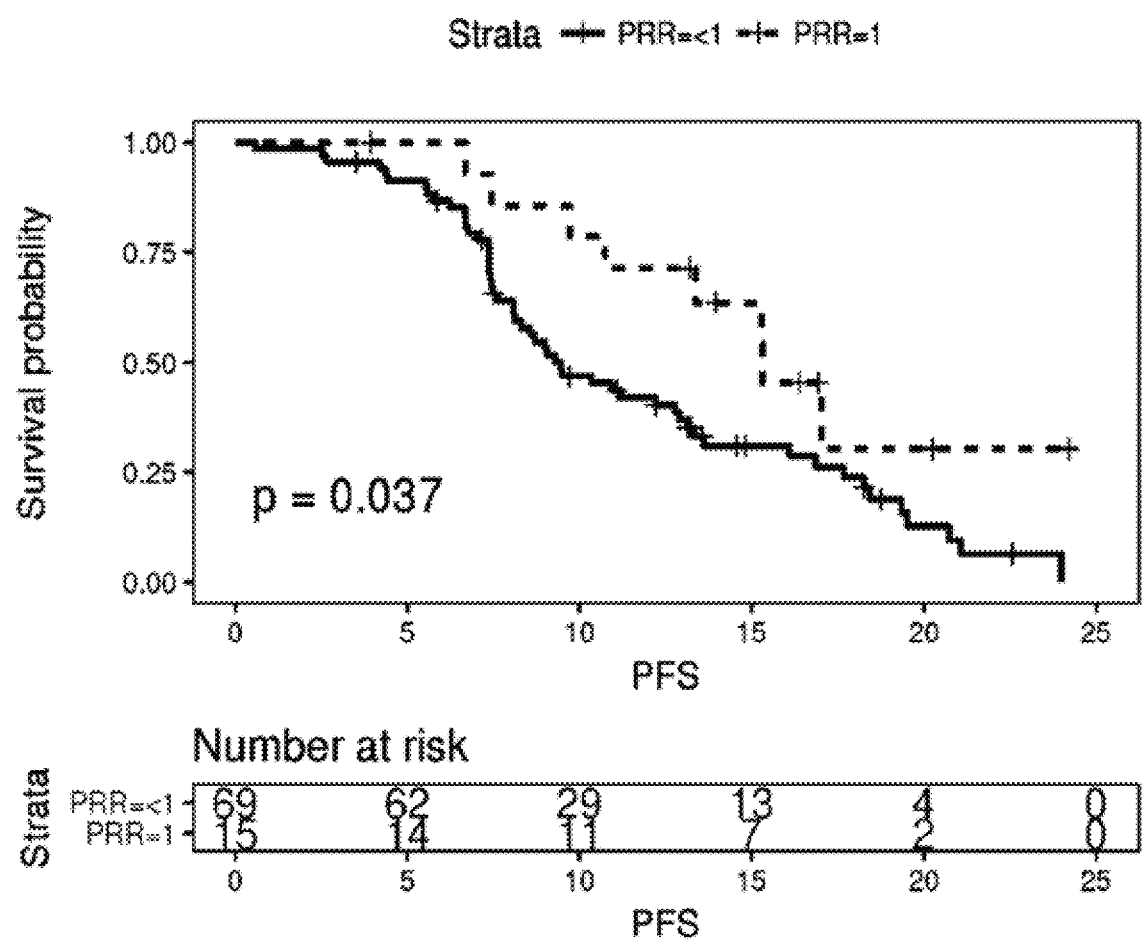
FIG. 3 is a Kaplan Meier graph of progression-free survival (PFS) of patients grouped by plasma recovery rate (PRR).

In some embodiments, the measure of plasma-tissue discordance is Plasma Recovery Rate (PRR). PRR is a ratio of shared plasma and matched tissue variants to total plasma variants. Complete tissue-plasma discordance and concordance were defined as PRR=0 and PRR=1, respectively. A PRR of 0 means that none of the variants observed in plasma was observed in tissue and is a strong indicator of heterogeneity and rapid cancer evolution, i.e. the metastatic clones share no variants with the primary tumor. An example of the use of PRR is shown in FIGS. 2 and 3.

In another embodiment, the invention is a method of treatment. The inventors have assessed tumor genetic heterogeneity (as PRR) in patients receiving irinotecan. Based on the assessment, the present invention includes a method of treatment of a cancer patient with irinotecan. The method includes a step of determining PRR. If PRR is high, irinotecan is administered to the patient.

In another embodiment, the invention is a method of treatment of a patient at risk for metastatic tumors, such as distant non-liver metastatic tumors. Based on the assessment of genetic heterogeneity, the present invention includes a method of metastasis-targeting treatment of a cancer patient. The method includes a step of determining genetic heterogeneity and if genetic heterogeneity is high, administering the metastasis-targeting treatment. In some embodiments, the metastasis-targeting treatment is irradiation of brain metastases. In some embodiments, the metastasis-targeting treatment is administering biphosphonates decreasing fractures caused by bone metastases. See Riihimaki et al., (2016) *Patterns of metastasis in colon and rectal cancer*, Scientific Reports volume 6, Article number: 29765 doi:10.1038/srep29765.

In some embodiments, the measure of plasma-tissue discordance is Tissue Recovery Rate (TRR), a ratio of shared plasma and matched tissue variants to total tissue variants. In some embodiments, the measure of plasma-tissue discordance is Jaccard Index (JI), a ratio of shared plasma and matched tissue variants to total variants detected in either plasma or tissue.

In some embodiments, measuring genetic heterogeneity comprises measuring plasma-based allelic fraction dispersion, which can be measured as Mutant-Allele Tumor Heterogeneity (MATH) including chromosomal-weighted MATH (cwMATH) and change in MATH or cwMATH from pre- to post-treatment.

In some embodiments, the measure of plasma-based allelic fraction dispersion is Mutant-Allele Tumor Heterogeneity (MATH). MATH is a measure of variant allele frequency dispersion, applied here to plasma. MATH is essentially a ratio of the width of the distribution to the center of the distribution, similar to the coefficient of variation, and was first defined in Mroz, E. A. & Rocco. J. W. *MATH, a novel measure of intratumor genetic heterogeneity, is high in poor-outcome classes of head and neck squamous cell carcinoma*. Oral Oncology (2013). MATH is calculated according to Formula 1.

$$MATH = 100 \times MAD/median(X)$$

$$MAD(\text{median absolute deviation}) = median(|Xi - median(X)|). \quad \text{Formula 1:}$$

Xi is the variant allele frequency (VAF) of the ith variant
median(X) is the median of all the VAFs of somatic variants in the sample.

Figure 4:
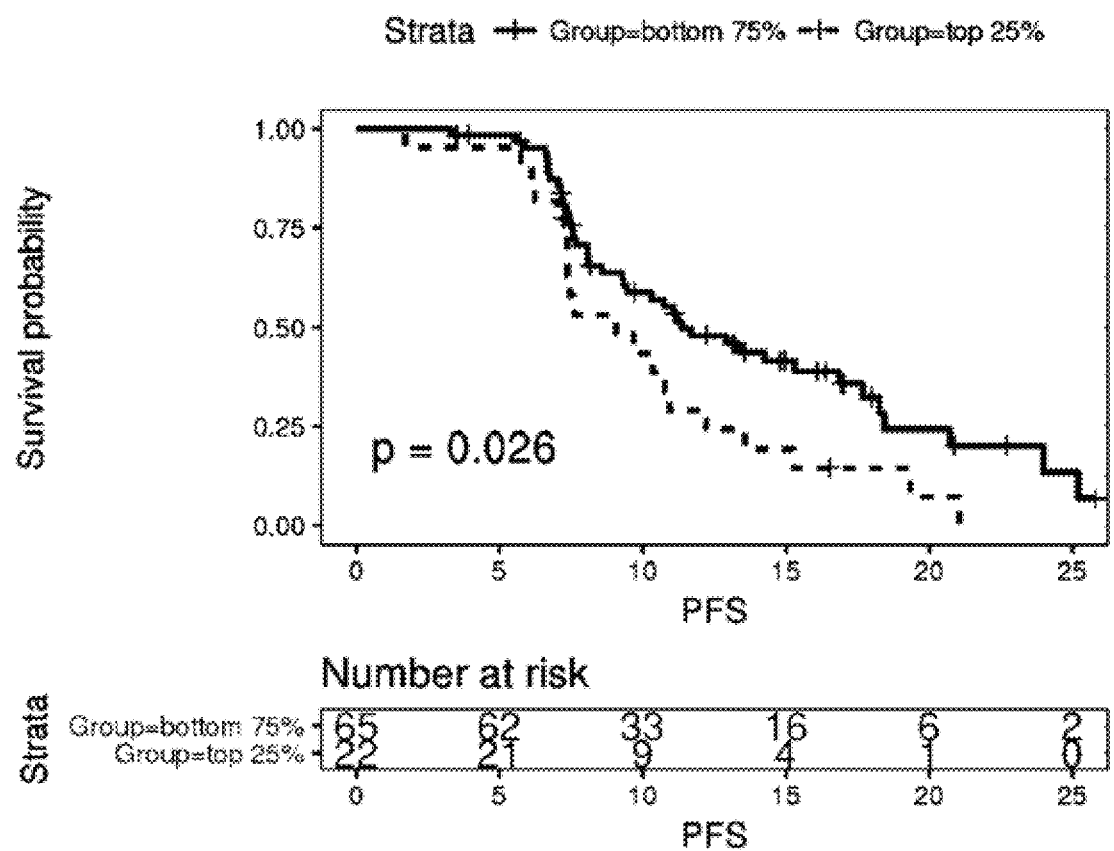
FIG. 4 is a Kaplan Meier graph of overall survival (OS) of patients grouped by mutant allele tumor heterogeneity (MATH) measured pre-therapy.
Figure 5:
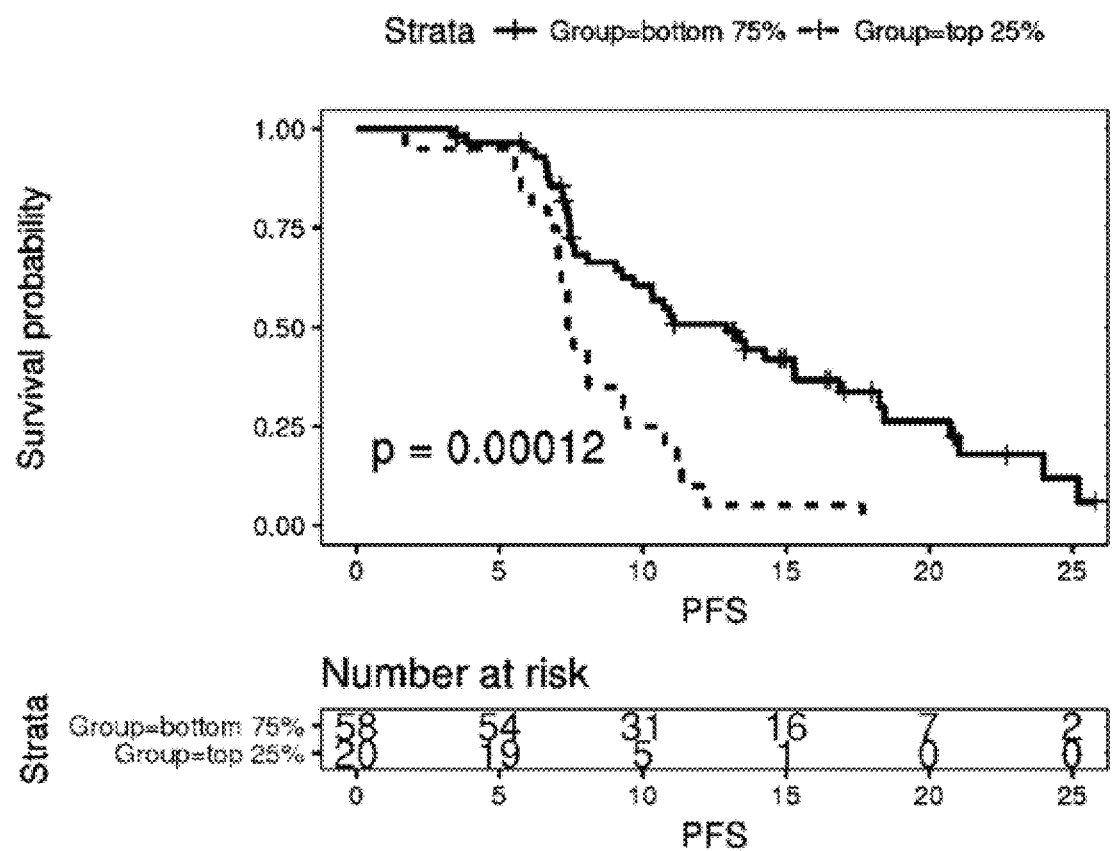
FIG. 5 is a Kaplan Meier graph of overall survival (OS) of patients grouped by mutant allele tumor heterogeneity (MATH) measured post-therapy.

MATH has been previously applied to solid tumors using whole exome sequencing data on tissue samples with matched normal. The inventors devised a method of using MATH on plasma samples without matched normal. The inventors found that patients with high plasma dispersion (MATH in the top quartile) had worse overall survival. An example of the use of MATH is shown on FIGS. 4 and 5.

In some embodiments, the method comprises a step of calling somatic versus germline single nucleotide variants or polymorphisms (SNVs or SNPs). The method further comprises a step of excluding homozygous SNVs (SNPs) and utilizing the heterozygous SNP (hetSNP) distribution to calculate background heterogeneity to calculate a modified score, called cwMATH. cwMATH corrects for allelic frequency dispersion that is driven solely by copy number variation and not subclonality.

In some embodiments, the measure of genetic heterogeneity is cwMATH determined according to Formula 2.

$$cwMATH = 100 \times \{median(CWscale|Xi - median(X)|)\}/median. \quad \text{Formula 2:}$$

In one example, CWscale and cwMATH are calculated using the following step
1. Calculate mean deviation of hetSNPs from 05 by chromosome for weights (CWscale). Mean was chosen instead of median to capture potentially focal CNVs that could affect sSNV (somatic SNV) AF, The mean deviation is defined as mean(abs(x−0.5)/0.5), where x is the hetSNP allele frequency, x ranges from 0 to 1. CWscale is 1−mean(abs(x−0.5)/0.5) so that a sSNV on a chromosome with higher hetSNP deviation from the expected 0.5 will be scaled closer back to the median in the MATH calculation.
   ii. Calculate median AF of sSNVs. Let this be median (sSNV.AFs).
   iii. Use CW to scale absolute deviation from median for each sSNVs. In other words, ScaledMedianAbsDev=abs(sSNV.AF−median(sSNV.AFs)) times (CWscale for that chr),
   iv. Take median of sSNV absolute deviations, divide by the median sSNV AF, and scale by 148.26(as in MATH). Mathematically, this is medianAbsDevMed=1.4826*median(ScaledMedianAbsDev) and cwMATH=100*medianAbsDevMed/median(sSNV.AFs).

In some embodiments, the measure of plasma-based allelic fraction dispersion is modified to utilize a log-scaled allelic fraction or other transformed allelic fraction prior to MATH or cwMATH.

In some embodiments, the measure of plasma-based allelic fraction dispersion is the change in MATH or cwMATH from pre- to post-treatment.

Figure 8:
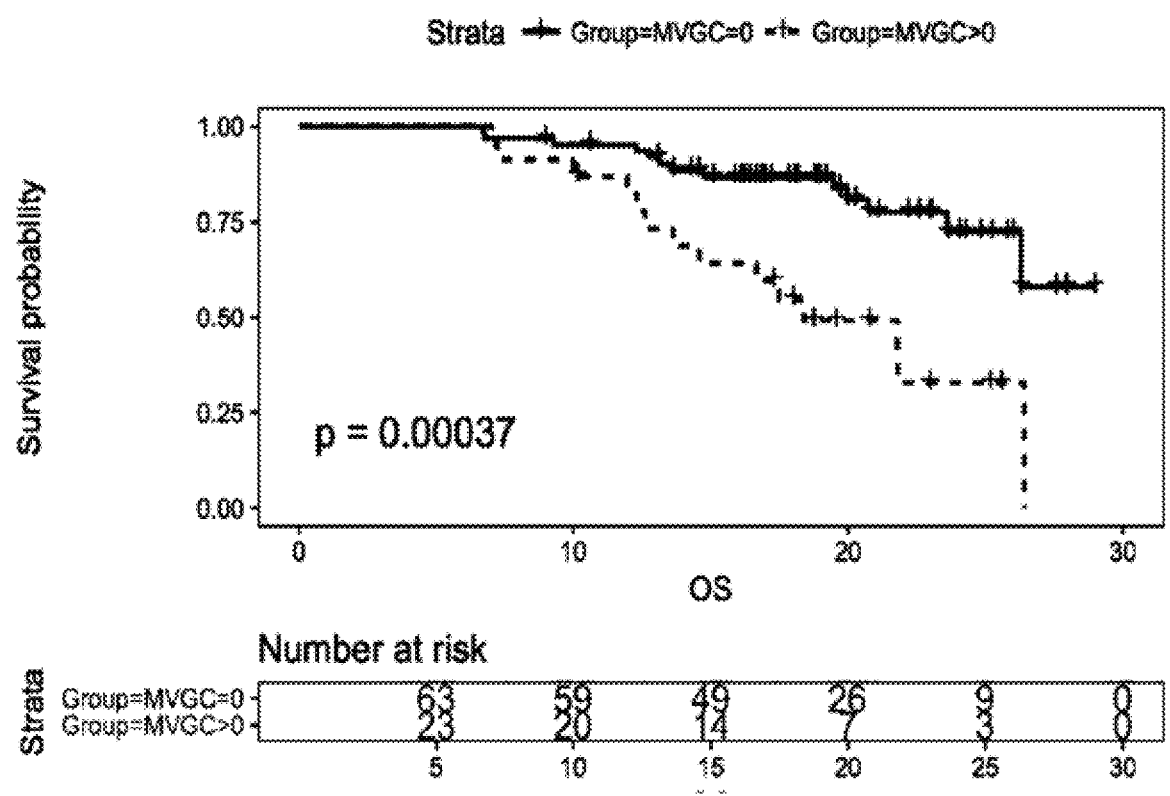
FIG. 8 is a Kaplan Meier graph of overall survival (OS) of patients grouped by multi-variant gene count (MVGC) measured post-therapy.

In some embodiments, measuring genetic heterogeneity comprises measuring intragenic variant heterogeneity measured as Multi-Variant Gene Count (MVGC), a count of genes with multiple mutations in plasma. This score could be >0 (i.e., at least one gene has more than one somatic mutation) because of heterogeneity (subclones harbor different mutations in the same gene) or homozygous somatic activation/inactivation, indicative of cancer adaptations. MVGC is a powerful global measure as it does not require the identification of a single resistance pathway/gene/variant but rather captures the potential of the cancer to genetically adapt to treatment. An example of the use of MVGC is shown on FIG. 8.

Figure 9:
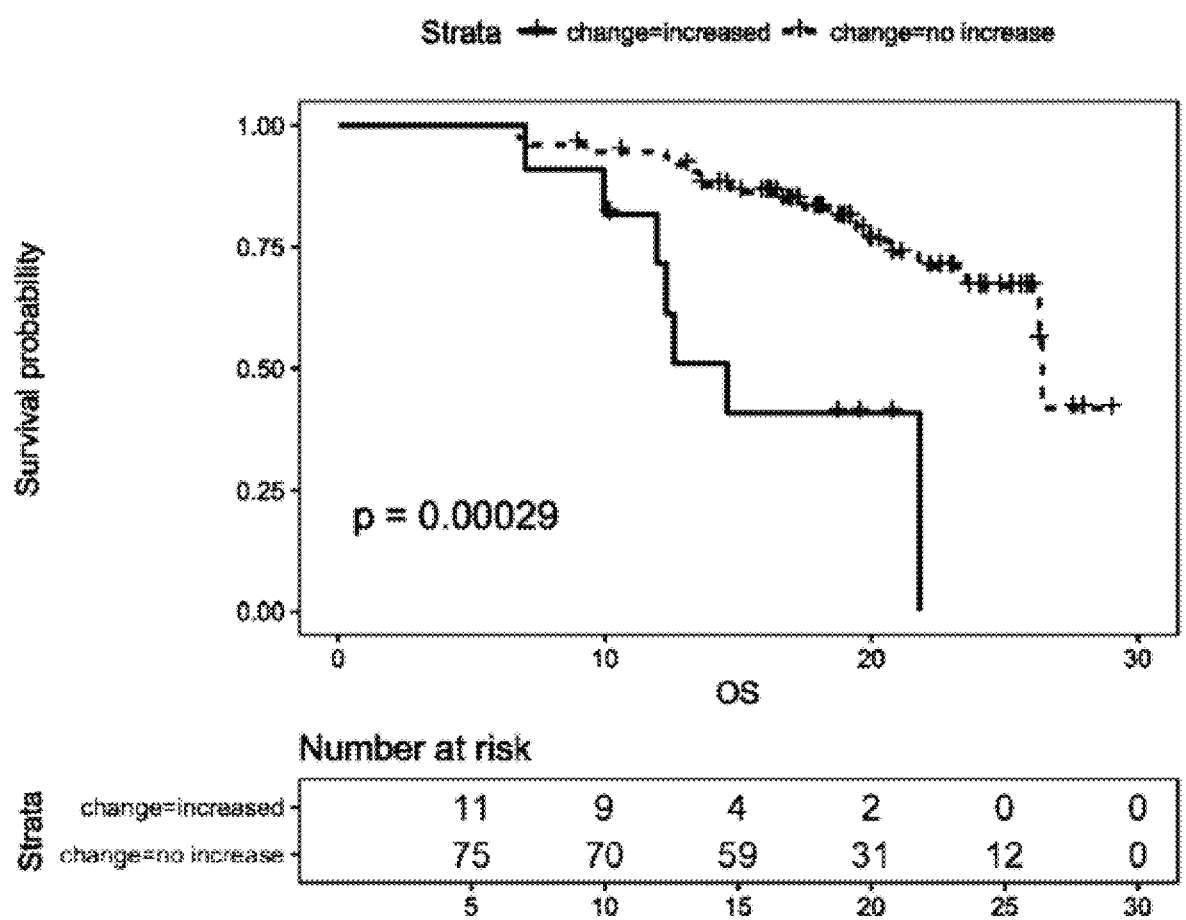
FIG. 9 is a Kaplan Meier graph of overall survival (OS) of patients grouped by increase in gene count (MVGC) between pre- and post-therapy measurements.

In some embodiments, measuring genetic heterogeneity comprises measuring change in MVGC from pre- to post-treatment. An example of the use of change in MVGC is shown on FIG. 9.

Figure 6:
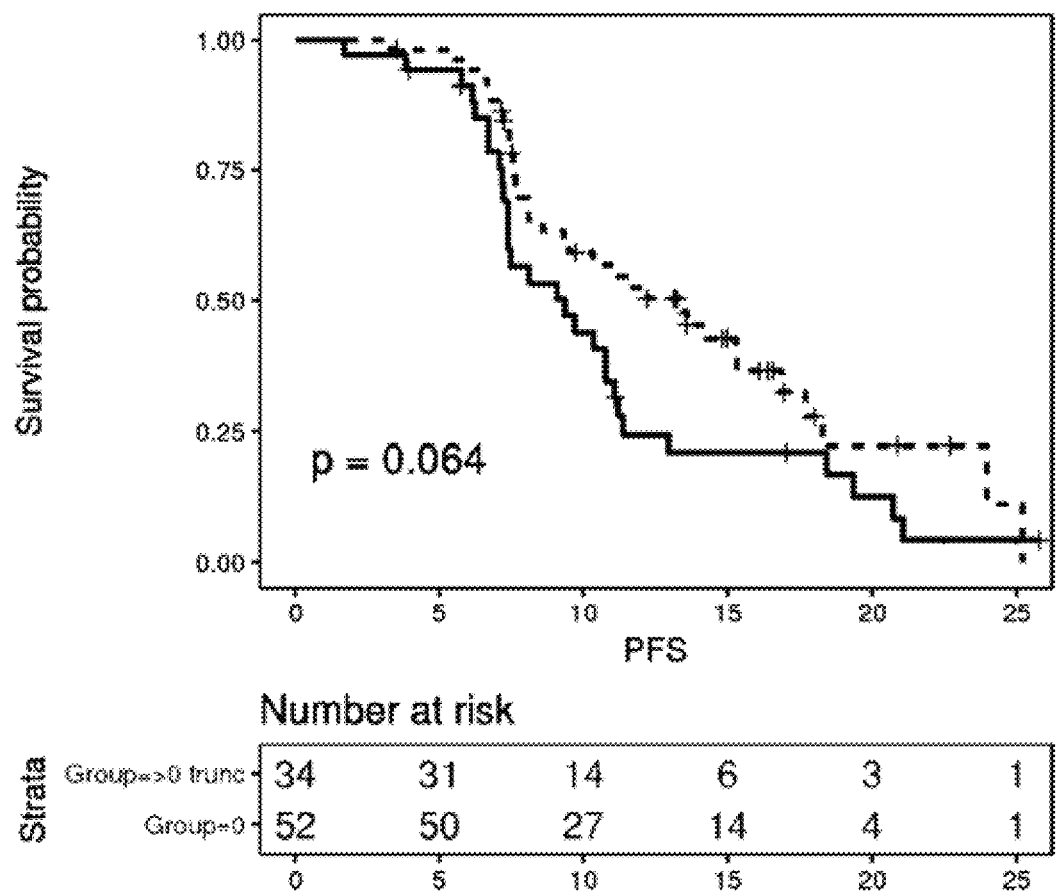
FIG. 6 is a Kaplan Meier graph of progression-free survival (PFS) of patients grouped by the presence of gene truncation mutations detected post-therapy.
Figure 7:
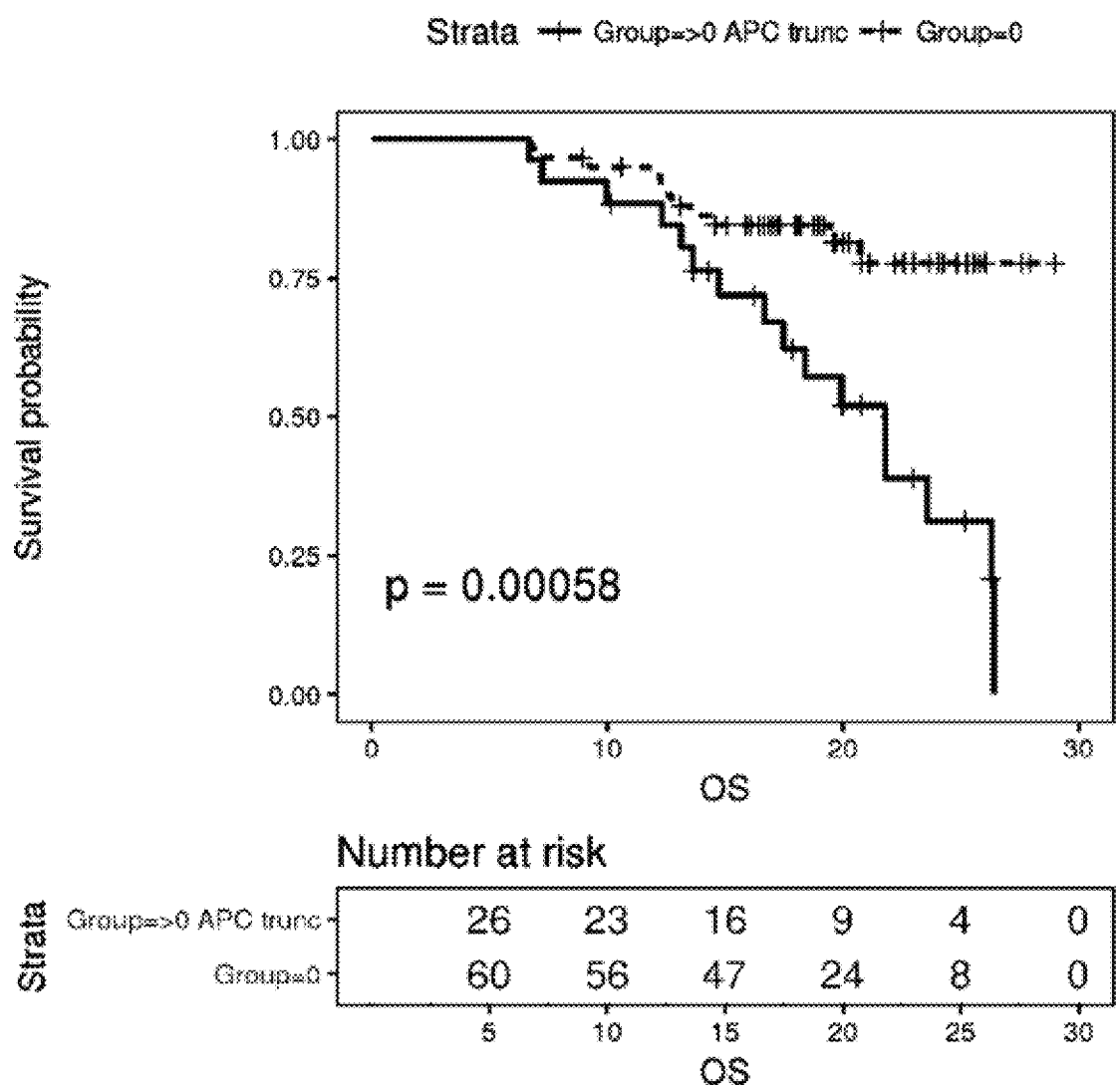
FIG. 7 is a Kaplan Meier graph of progression-free survival (PFS) of patients grouped by the presence of truncation mutations in APC gene detected post-therapy.

In some embodiments, measuring genetic heterogeneity comprises measuring truncation mutations in genes. In some embodiments, the genes include one or more of TP53, FBXW7, and APC. In some embodiments, gene truncations are measured only in plasma without a solid tumor tissue sample. In some embodiments, gene truncations are measured only in post-therapy (post-induction) plasma. An example of the use of truncation mutations is shown on FIGS. 6 and 7.

Analyses of ctDNA performed with AVENIO ctDNA Kits on CRC patients in the STEAM clinical trial revealed the potential prognostic value of measuring plasma-based intra-tumor heterogeneity. The inventors discovered that pre-induction, greater tissue-plasma discordance and high plasma dispersion correlated with shorter survival. Post-induction, high plasma dispersion and intragenic heterogeneity also correlated with shorter survival. Truncating APC mutations in post-induction plasma also correlated with shorter survival and could be a biomarker for metastases. Accordingly, in some embodiments, the invention is a method of treatment of a patient having cancer comprising a step of administering additional amount of therapeutic agent (maintaining the current treatment) or administering a different therapeutic agent after the step of assessing the change in tumor genetic heterogeneity by measuring one or more of PRR. MATH or MVGC. The method of the invention may complement current methods to assess-treatment efficacy, including change in blood carcinoembryonic antigen (CEA) levels and radiologically assessed changes in the sizes of the primary tumor and metastases.

EXAMPLES

Example 1. Using Cell-Free Tumor DNA and Solid Tumor DNA of Metastatic Colorectal Cancer (mCRC) Patients to Detect Mutations In this example, samples from STEAM clinical trial were used. STEAM (NCT01765582) evaluated the efficacy and safety of concurrent (c) and sequential(s) FOLFOXIRI-bevacizumab (BEV) versus FOLFOX-BEV for first-line treatment of mCRC. The next-generation sequencing based AVENIO® ctDNA Expanded and Surveillance Kits (Roche Sequencing Solutions, Pleasanton, Cal.) were used to identify somatic mutations and mutation burden. The Expanded Kit was used to analyze 77 cancer-related genes by next-generation sequencing (NGS) in tissue, and pre- and post-induction plasma samples (n=182, 150, and 118, respectively). The Surveillance Kit was used to profile somatic mutations in 197 cancer-related genes in pre- and post-induction plasma samples.

Example 2. Using Mutation Status to Determine Tumor Heterogeneity

Variants detected by both kits as described in Example 1 were aggregated to calculate tumor heterogeneity. Heterogeneity was measured as tissue-plasma discordance, plasma-based intra-tumor mutant allele fraction dispersion, intergenic variant heterogeneity, and the presence of multiple APC truncating mutations.

Plasma-based intra-tumor heterogeneity was calculated by measuring plasma-tissue discordance measured as Plasma Recovery Rate (PRR), a ratio of shared plasma and matched tissue variants to total plasma variants. Complete tissue-plasma discordance and concordance were defined as PRR=0 and PRR=1, respectively. A PRR of 0 means that none of the variants observed in plasma was observed in tissue and is a strong indicator of heterogeneity and rapid cancer evolution, i.e. the metastatic clones share no variants with the primary tumor. Patients were grouped by PRR to assess survival (See results on FIGS. 2 and 3).

Plasma-based allelic fraction dispersion was measured as Mutant-Allele Tumor Heterogeneity (MATH) pre- and post-treatment. Patients were grouped by MATH to assess survival (See results on FIGS. 4 and 5).

Intragenic variant heterogeneity was measured as Multi-Variant Gene Count (MVGC) and change in MVGC from pre- to post-treatment. (See results on FIGS. 8 and 9).

Changes in specific molecular markers were measured as truncating mutations in any gene or in the APC gene specifically, and as a change in number of truncating mutations from pre- to post-treatment. (See results on FIGS. 6 and 7).

Subjects with complete tissue-plasma concordance, suggestive of clonality and limited cancer evolution, had longer PPS (18.3 vs 9.5 mo, HR 0.43, logrank p=0.037). Complete tissue-plasma discordance had some association with non-liver limited disease (p=0.0895), which is known to be associated with poorer prognosis (Riihimaki et al., *Metastic spread in patients with gastric cancer*. Oncotarget. 2016 Aug. 9; 7(32):52307-52316). Subjects with high pre-Induction or post-induction plasma MATH had shorter PFS (8.1 vs 11.7 mo. HR 1.8, logrank p=0.026; 7.4 vs 12.2 mo, HR 2.9, logrank p=0.00012, respectively). Similar trends were seen for OS. Subjects with intragenic plasma heterogeneity post-induction also had shorter OS, and those with an increase in MVGC from pre- to post-induction plasma had shorter OS (14.8 vs 26.4 mo, HR 4.6, logrank p=0.00029). Truncating APC mutations correlated with shorter PFS (7.6 vs. 12.2 mo, HR 2.3, logrank p=0.0017) and was significantly associated with high post-induction MATH (logrank p a 0.006), consistent with an accumulation of genetically diverse metastases. The role of APC mutation count and metastatic potential in primary tumors has been studied (Schell. M. J. et al. *A multigene mutation classification of 468 colorectal cancers reveals a prognostic role for APC*. Nat Commun. 2016 Jun. 15; 7:11743) and of particular interest in this context is that the accumulation of new APC truncating mutations in post treatment plasma samples appears to correlate with the rate of progression of metastatic spread.

Example 3. Using Tumor Heterogeneity to Determine Treatment Protocol

Figure 10:
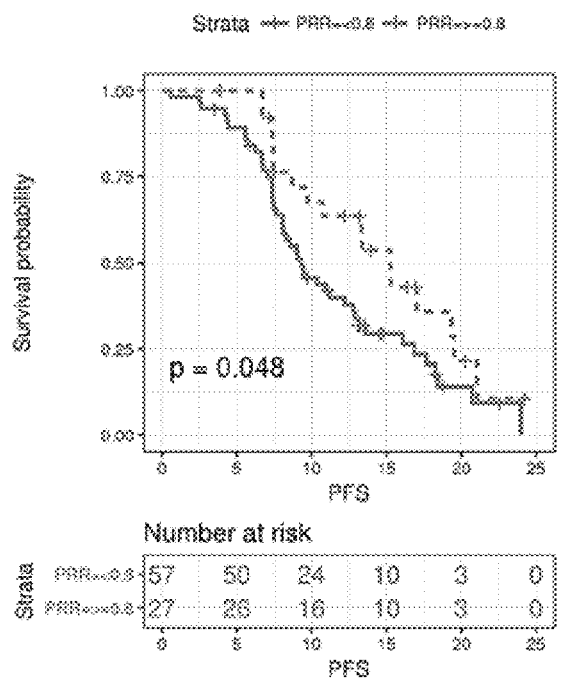
FIG. 10 is a Kaplan Meier graph of progression-free survival (PFS) and overall survival (OS) of patients grouped by plasma recovery rate (PRR) with 0.8 cut-off.
Figure 10:
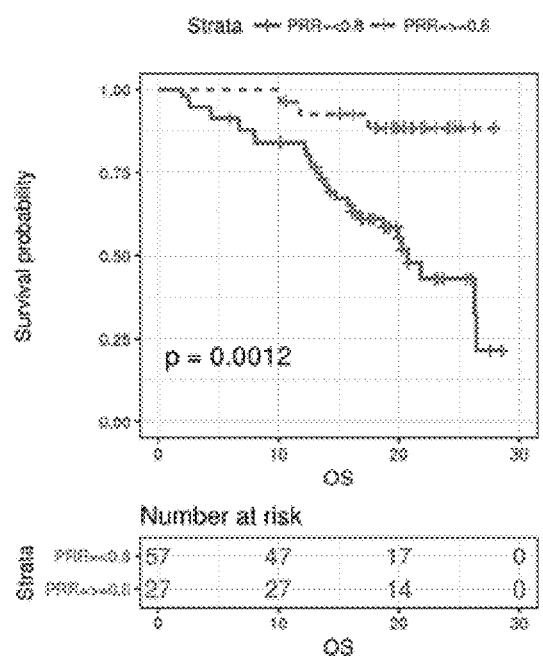
Figure 11:
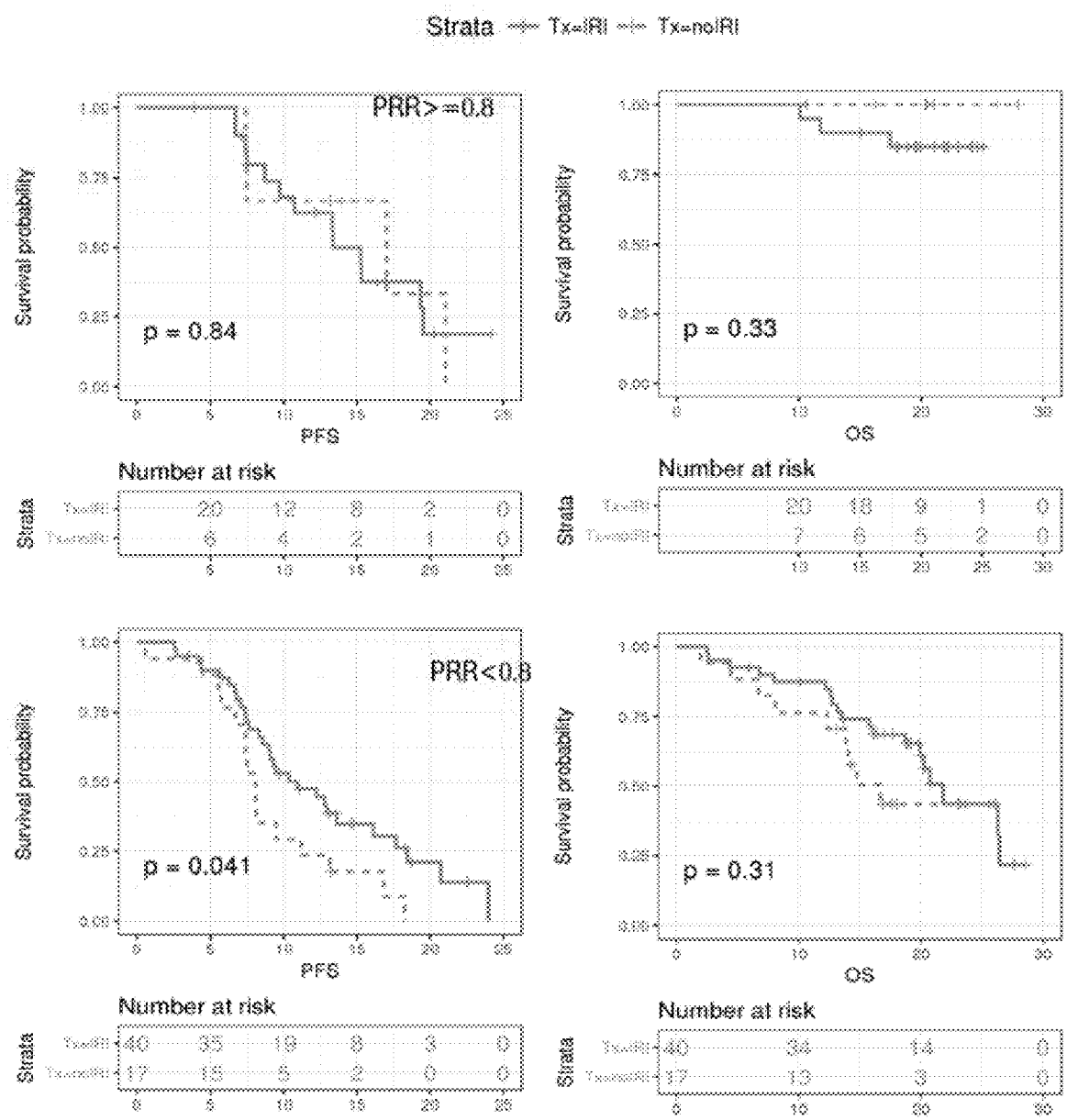
FIG. 11 is a Kaplan Meier graph of progression-free survival (PFS) overall survival (OS) of patients grouped by PRR with 0.8 cut-off and also by therapy regimen.

Plasma Recovery Rate (PRR), was measured as described in Example 2. Heterogeneity was defined as PRR<0.8 (low) and PRR>=0.8 (high) (See results on FIG. 10). Patients were grouped by PRR and further grouped by therapy regimen: with and without irinotecan to assess survival as PFS and OS (FIG. 11). Based on the results (FIG. 11), irinotecan is indicated for high heterogeneity (PRR high) and not indicated for low heterogeneity (PRR low.)

We claim:

1. A method for identifying a cancer patient as likely to positively respond to a therapy regimen, the method comprising the steps of:
   (a) providing samples obtained from the patient comprising at least one solid tumor sample and at least one blood plasma sample;
   (b) determining in the samples the sequence of at least a portion of each of the biomarkers APC, KRAS, ABL1, FGFR3, JAK3, RAF1, BRCA1, MET, AKT1, FLT1, KDR, RNF43, BRCA2, TP53, AKT2, FLT3, MAP2K1, TERT promoter, EGFR, KIT, ARAF, FLT4, MAP2K2, TSC1, ERBB2, NRAS, CDK6, GATA3, MTOR, TSC2, ALK, PDGFRA, CSF1R, GNA11, NFE2L2, PTEN, BRAF, RET, CTNNB1, GNAQ, NTRK1, RB1, DPYD, ROS1, DDR2, GNAS, PDGFRB, SMAD4, AR, MSH2, EZH2, IDH1, PIK3CA, SMO, CCND1, MSH6, FGFR1, IDH2, PIK3R1, STK11, CCND2, NF2, FGFR2, JAK2, PTCH1, VHL, CCND3, PDCD1LG2, CDK4, ESR1, KEAP1, UGT1A1, CD274, PMS2, CDKN2A, FBXW7, and MLH1;
(c) determining a measure of tissue-plasma genetic heterogeneity in the biomarker sequence, the measure of genetic heterogeneity selected from plasma recovery rate (PRR) and multi-variant gene count (MVGC);
(d) identifying the patient as likely to positively respond to a less aggressive therapy regimen if the measure of genetic heterogeneity is low and administering the less aggressive therapy regimen; or
(e) identifying the patient as not likely to positively respond to a less aggressive therapy regimen if the measure of genetic heterogeneity is high and administering a more aggressive therapy regimen,
wherein the measure of genetic heterogeneity is low for PRR<0.8 or MVGC=0, and wherein the measure of genetic heterogeneity is high for PRR≥0.8 or MVGC>0,
wherein the cancer is selected from among non-small cell lung cancer (NSCLC) and colorectal cancer (CRC) in stages I, II, III and IV,
wherein the positive response to therapy is selected from increased progression free survival (PFS) and increased overall survival (OS),
wherein, the more aggressive therapy regimen comprises at least one of a higher dose of therapy, addition of one or more therapeutic agents, and extended duration of therapy as compared to the less aggressive therapy regimen.

2. The method of claim 1, wherein the therapy regimen is selected from treatment with FOLFOXIRI-bevacizumab and treatment FOLFOX-bevacizumab.

3. The method of claim 1, wherein the plasma samples obtained from the patient comprise at least two samples, wherein the samples collected during more than one time point selected from pre-, during- and post-chemotherapy, and wherein the measure of genetic heterogeneity is compared between time points.

4. A method of treatment of a non-small cell lung cancer (NSCLC) or colorectal cancer (CRC) patient in stage II, III or IV comprising the steps of:
(a) providing samples obtained from the patient comprising at least one solid tumor sample and at least one blood plasma sample;
(b) determining in the samples the sequence of at least a portion of each of the biomarkers APC, KRAS, ABL1, FGFR3, JAK3, RAF1, BRCA1, MET, AKT1, FLT1, KDR, RNF43, BRCA2, TP53, AKT2, FLT3, MAP2K1, TERT promoter, EGFR, KIT, ARAF, FLT4, MAP2K2, TSC1, ERBB2, NRAS, CDK6, GATA3, MTOR, TSC2, ALK, PDGFRA, CSF1R, GNA11, NFE2L2, PTEN, BRAF, RET, CTNNB1, GNAQ, NTRK1, RB1, DPYD, ROS1, DDR2, GNAS, PDGFRB, SMAD4, AR, MSH2, EZH2, IDH1, PIK3CA, SMO, CCND1, MSH6, FGFR1, IDH2, PIK3R1, STK11, CCND2, NF2, FGFR2, JAK2, PTCH1, VHL, CCND3, PDCD1LG2, CDK4, ESR1, KEAP1, UGT1A1, CD274, PMS2, CDKN2A, FBXW7, and MLH1;
(c) determining a measure of tissue-plasma genetic heterogeneity in the biomarker sequence, the measure of heterogeneity selected from plasma recovery rate (PRR), mutant allele tumor heterogeneity (MATH) without matched normal, and multi-variant gene count (MVGC);
(d) identifying the patient as likely to positively respond to a less aggressive therapy regimen if the measure of genetic heterogeneity is low and administering the less aggressive therapy regimen; or
(e) identifying the patient as not likely to positively respond to a less aggressive therapy regimen if the measure of genetic heterogeneity is high and administering a more aggressive therapy regimen,
wherein, the more aggressive therapy regimen comprises at least one of a higher dose of therapy, addition of one or more therapeutic agents, and extended duration of therapy as compared to the less aggressive therapy regimen,
wherein the measure of genetic heterogeneity is low for PRR<0.8, MATH in the bottom 75% for a corresponding group of NSCLC or CRC patients, or MVGC=0, and wherein the measure of genetic heterogeneity is high for PRR≥0.8, MATH in the top 25% for a corresponding group of NSCLC or CRC patients, or MVGC>0,
wherein the positive response to therapy is selected from increased progression free survival (PFS) and increased overall survival (OS).

5. A method of treatment of a non-small cell lung cancer (NSCLC) or colorectal cancer (CRC) patient in stage II, III or IV comprising the steps of:
(a) providing samples obtained from the patient comprising at least one solid tumor sample and at least one blood plasma sample;
(b) determining in the samples the sequence of at least a portion of each of the biomarkers APC, KRAS, ABL1, FGFR3, JAK3, RAF1, BRCA1, MET, AKT1, FLT1, KDR, RNF43, BRCA2, TP53, AKT2, FLT3, MAP2K1, TERT promoter, EGFR, KIT, ARAF, FLT4, MAP2K2, TSC1, ERBB2, NRAS, CDK6, GATA3, MTOR, TSC2, ALK, PDGFRA, CSF1R, GNA11, NFE2L2, PTEN, BRAF, RET, CTNNB1, GNAQ, NTRK1, RB1, DPYD, ROS1, DDR2, GNAS, PDGFRB, SMAD4, AR, MSH2, EZH2, IDH1, PIK3CA, SMO, CCND1, MSH6, FGFR1, IDH2, PIK3R1, STK11, CCND2, NF2, FGFR2, JAK2, PTCH1, VHL, CCND3, PDCD1LG2, CDK4, ESR1, KEAP1, UGT1A1, CD274, PMS2, CDKN2A, FBXW7, and MLH1;
(c) determining a measure of tissue-plasma genetic heterogeneity in the biomarker sequence as plasma recovery rate (PRR);
(d) administering irinotecan if PRR is ≥0.8.

* * * * *